United States Patent
Hulko et al.

(10) Patent No.: US 8,252,606 B2
(45) Date of Patent: Aug. 28, 2012

(54) SENSOR FOR THIOL ANALYTES

(75) Inventors: Michael Hulko, Stuttgart (DE); Ingeborg Hospach, Stuttgart (DE); Gabriele Nelles, Stuttgart (DE); Jens Ulmer, Stuttgart (DE)

(73) Assignee: Sony Corporation, Tokyo (JP)

( * ) Notice: Subject to any disclaimer, the term of this patent is extended or adjusted under 35 U.S.C. 154(b) by 351 days.

(21) Appl. No.: 12/574,511

(22) Filed: Oct. 6, 2009

(65) Prior Publication Data

US 2010/0231899 A1    Sep. 16, 2010

(30) Foreign Application Priority Data

Oct. 6, 2008  (EP) .................................. 08017510
Mar. 31, 2009  (EP) .................................. 09004766

(51) Int. Cl.
*G01N 27/00*  (2006.01)
(52) U.S. Cl. .................. 436/518; 436/149; 356/218
(58) Field of Classification Search .................. 436/149, 436/145, 169, 518; 356/432–440, 218
See application file for complete search history.

(56) References Cited

U.S. PATENT DOCUMENTS

2003/0166295 A1   9/2003   Fukuoka et al.
2004/0099536 A1*  5/2004   Srinivasan et al. ............. 205/317
2007/0235760 A1* 10/2007   Shim et al. ..................... 257/192

FOREIGN PATENT DOCUMENTS

WO   WO 00/65347   11/2000

OTHER PUBLICATIONS

Liu et al: "A highly sensitive biosensor with (Con A/HRP)n multilayer films based on layer-by-layer technique for the detection of reduced thiols" Biosensors & Bioelectronics, Elsevier Science Publishers, Barking, GB, vol. 22, No. 12, May 16, 2007, pp. 3210-3216, XP022080465.

Yu et al: "Development of amperometric horseradish peroxidase based biosensors for clozapine and for the screening of thiol compounds" Biosensors & Bioelectronics, Elsevier Science Publishers, Barking, GB, vol. 22, No. 11, Mar. 30, 2007, pp. 2707-2711, XP022006477.

Chinese Office Action issued Jun. 9, 2011, in Patent Application No. 200910221408.0 (with English-language translation).

* cited by examiner

*Primary Examiner* — Hoa Pham
(74) *Attorney, Agent, or Firm* — Oblon, Spivak, McClelland, Maier & Neustadt, L.L.P.

(57) ABSTRACT

The present invention relates to a sensor for thiol analytes, to a sensor array and to a method of detecting thiol analytes using said sensor.

20 Claims, 19 Drawing Sheets

Sensor principle

SENSOR FOR THIOL ANALYTES

The present invention relates to a sensor for thiol analytes, to a sensor array and to a method of detecting thiol analytes using said sensor.

Nowadays, thiol detection is used in different fields, such as: medical applications to examine physical conditions or disorders related to thiol compounds. Sources of indicative thiol compounds can be breath, saliva, blood, urine, plasma, cerebrospinal fluids or pus. For instance, breath analysis can be used to detect halitosis, in the food industry for analysis of food freshness or process analysis, and for stationary and mobile environmental monitoring (waters, waste water, air).

The instruments used for thiol analysis are for example:

Analytical Methods
  Gas-chromatography combined with mass spectrometry. Complex mixtures of volatile compounds can be analyzed. Different substances are separated by chromatography and subsequently identified by mass spectrometry. These instruments are usually very expensive and require a high degree of expertise to operate them.
Chemical Sensors
  Gas-chromatography combined with gas sensors
  Various electronic nose (eNose) devices that comprise chemical sensors or sensor-arrays. There are several laboratory-based devices and prototypes.
  Metal oxide sensors
  Electrochemical devices based on amperometry
  Conductive polymers
  QCM devices based on mass-sensitive piezosensors coated with polymers
  Organic dyes and optical detection
Biosensors (Typically Used in Liquid Phase)
  Enzyme catalyzed reactions and detection of the appearance of products or consumption of educts thereof; e.g. with flavin-containing monooxygenase or with monoamine oxidase or with sulfhydryl oxidase.
  Enzyme, like horseradish peroxidase, that catalyse a measurable reaction which is interfered by thiols. Thereby thiols react with an intermediate state of the enzyme and reduce its apparent activity.
  Biosensors made for other analytes than thiols with similar detection principle (typically in liquid phase):
    E.g. Glucose oxidase which is used for sensing its physiological substrate glucose. Detection is realized by counting electrons transferred from glucose to the cofactor FAD For advanced thiol sensors in applications, sensors have to operate reliably in complex environments and detect thiol compounds even in the presence of other chemicals like amines, alcohols or water. Many chemical sensors respond to thiol as well as to other compounds due to cross-reactivity. Such cross-reactivity can for example be reduced or avoided by previous separation steps that require additional hardware, other than the sensor itself. Another possibility is to measure the cross-reactivity itself by sensor arrays and pattern-recognition algorithms. Yet another approach in the prior art was to use enzymes which provide a specific recognition for thiol analyte detection of complex mixtures. Enzymatic thiol detection approaches are based on thiol conversion reactions and a catalytic use of an enzyme. The generation of products or the consumption of educts is indicative of the presence and/or amount of thiols in a sample. In any case, however, this approach demands the controlled presence of certain co-reactants within the device and specific reaction conditions.

Accordingly, it was an object of the present invention to provide for a sensor for detecting thiol analytes which is capable of detecting thiols even in the presence of other compounds. It was also an object of the present invention to provide for a sensor for thiol analytes which shows no or very little cross-reactivity. Moreover, it was an object of the present invention to provide for a sensor for thiol analytes which operates in complex environments. It was also an object of the present invention to provide for a sensor which can be used for analytes in the gas and the liquid phase. It was also an object of the present invention to provide for a sensor which allows a real-time analysis. It was also an object of the present invention to provide for a sensor which omits the need for any co-reactants to be measured. It was also an object of the present invention to provide for a sensor which is adaptable to a variety of analytes.

All these objects are solved by a sensor for thiol analytes, comprising:

a redox active protein, which, upon interaction with a thiol analyte, undergoes a change in a physical property, a transducer, which, upon said change in said physical property of said redox active protein, converts said change in said physical property into an electrical signal.

In one embodiment, said redox active protein is directly connected with said transducer. The term "directly connected", as used herein, is meant to refer to a direct physical contact between said protein and said transducer. Examples thereof are an immobilization of the protein on said transducer.

In one embodiment, said transducer converts said change in said physical property of said redox active protein without involving or using an electron mediator compound, such as hydroquinone.

In one embodiment said physical property is selected from the group of redox state, electrical conductivity/resistivity, current, potential, capacity, light absorbance, light transmittance, reflectivity, refractive index, fluorescence, phosphorescence, luminescence, mass as determined by gravimetry or mass-sensitive resonance techniques, heat as determined by calorimetry, conformation and physiological activity of said protein.

In one embodiment said redox active protein is a protein that is capable of reversibly transferring electrons.

In one embodiment said redox active protein is selected from the group comprising proteins in which a disulfide bond between two cystein residues can be reversibly formed, such as thioredoxin, proteins having prosthetic groups such as flavin adenine dinucleotide (FAD) as in monoamine oxidase, nicotinamide adenine dinucleotide (NAD), nicotinamide adenine dinucleotidephosphate (NADP), and flavin mononucleotide (FMN), metalloproteins comprising copper, such as superoxide dismutase, metalloproteins containing a non-heme-iron, such as ferredoxin,
metalloproteins containing heme-bound iron, such as cytochrome c, horseradish peroxidase, myoglobin, hemoglobin, catalase, membrane proteins comprising redox active groups such as cytochrome c oxidase.

In one embodiment said physical property is light absorbance, light transmittance, reflectivity, refractive index, fluorescence, phosphorescence, or luminescence, and said transducer converts said change in light absorbance, light transmittance, reflectivity, refractive index, fluorescence, phosphorescence, or luminescence into an electrical signal, wherein said transducer is a photometer or spectrophotometer or other device to measure light intensity or any of the aforementioned optical properties.

In the embodiment, wherein said physical property is light absorbance or any of the aforementioned other optical properties, the redox active protein is preferably immobilized on a transparent or reflective electrode, or it is immobilized on an electrically non-conducting transparent or reflective substrate, such as glass. An example of a transparent electrode would be fluorine-doped tin oxide (FTO) or indium-doped tin oxide (ITO). In these "optical" embodiments, a change of any of the aforementioned optical properties may be converted into an electrical signal, and, optionally, if there is a change in redox state, such change may additionally be converted into an electrical signal too.

In one embodiment said physical property is the redox state of said protein, and wherein said transducer converts said change in said redox state into an electrical signal, wherein said transducer is an electrode upon which said redox active protein has been immobilized, wherein said immobilization preferably occurs via chemisorption or physisorption.

In one embodiment said electrode is made of a material selected from metals such as gold, alloys, metal oxides such as tin oxide, e.g. FTO or ITO, carbon such as graphite or carbon nanotubes, electrically conducting polymers such as polyaniline, or composite materials such as organically interlinked metal nanoparticle films.

In one embodiment said redox active protein is present within said sensor in a first layer or in a spot or a plurality of spots, wherein, preferably, said redox active protein is immobilized in said first layer on an electrode or an electrically non-conducting substrate, wherein, more preferably, said electrode is a transducer as defined above. In one embodiment, said sensor further comprises a coating layer which covers said first layer or said spot or said plurality of spots, wherein said coating layer comprises an enzyme, said enzyme being capable of converting a redox inactive analyte into a redox active compound, or said enzyme, upon reaction with a redox inactive analyte, such as thiol, alcohol, being capable or producing a redox active compound, such as $H_2O_2$, NAD/NADH, NADP/NADPH, wherein, preferably, said redox active protein, upon interaction with said redox active compound undergoes a change in a physical property, as defined above.

In one embodiment, said coating layer is made of a polymeric material selected from polysaccharides such as starch, agarose, alginate, chitosan, gummi arabicum, polypeptides such as gelatine, and non-polysaccharidic, non-polypeptidic polymers such as polyacrylamide, polyacrylates, polyamides, polyesters, polyamines, polyoxides, polysulfones, polystyrenes, polyether, polyimines or any combination of mentioned polymers.

In one embodiment, said enzyme in said coating layer is different from said redox active protein in said first layer and is, preferably, selected from thiol oxidase, alcohol oxidase, amine oxidase, aldehyde oxidase, sulfite oxidase, nucleosid oxidase, hexose oxidase, amino acid oxidase, nitroalkane oxidase, ethanolamin oxidase, choline oxidase, retinal oxidase, thiamine oxidase, putrescine oxidase, sarcosine oxidase, pyruvat oxidase, malat oxidase, glyoxylat oxidase, oxalat oxidase, lactate oxidase, cholesterol oxidase, ecdysone oxidase, superoxide dismutase, carbonyl dehydrogenase, carboxylic acid reductase, toluene dioxygenase, nitrous oxide reductase, nitric oxide reductase, and nitrogen oxide reductase.

In one embodiment said thiol analyte is selected from the group comprising $C_1$-$C_{20}$ aliphatic thiols, aromatic thiols, side chains of amino acids such as cysteine, sidechains of polypeptides having a thiolgroup, such as gluthatione, thiol compounds dissolved in a solvent, and volatile thiols in the gas phase.

The objects of the present invention are also solved by a sensor array, comprising a plurality of sensors as defined above.

The objects of the present invention are also solved by a method of detecting a thiol analyte, comprising exposing a sensor according to the present invention or a sensor array according to the present invention to a sample suspected of containing a thiol analyte, measuring the presence or absence of an electrical signal generated by the transducer upon changes of said physical properties, wherein the presence and magnitude of the electrical signal is indicative of the presence and amount of a thiol analyte in said sample.

In one embodiment said sample contains, in addition to one or several thiol analytes, also other chemicals, such as amines, alcohols, aldehydes, ketones, carboxylic acids, hydrocarbons, halogenated hydrocarbons, or water, or mixtures of said other chemicals.

In one embodiment said sample is gaseous, liquid or solid.

The objects of the present invention are also solved by the use of the method according to the present invention for medical diagnosis, healthcare diagnosis, food quality testing, agricultural testing, security testing for explosives, toxins or harmful chemical substances, and/or for environmental monitoring.

The objects of the present invention are also solved by a method of changing the specificity of a sensor from one analyte to another analyte, said method comprising:
a) providing a sensor according to the present invention, but without a coating layer,
b) applying a coating layer to said sensor, said coating layer comprising an enzyme, said coating layer and said enzyme being as defined above.

In one embodiment, the method further comprises the steps:
c) removing said coating layer and said enzyme from said sensor, and
d) applying another coating layer to said sensor, said other coating layer comprising another enzyme, said other coating layer and said other enzyme being as defined above, but being different to the coating layer and enzyme of step b).

The objects of the present invention are also solved by a kit comprising the sensor according to the present invention, but without coating layer, and means to apply a coating layer on said sensor, said coating layer comprising an enzyme, said coating layer being as defined above, said enzyme being as defined above, wherein said means include polymeric material, as defined above, and said enzyme.

The objects of the present invention are also solved by a method of detecting an analyte, comprising exposing a sensor which comprises a coating layer according to the present invention or a sensor array of such sensors to a sample suspected of containing an analyte, measuring the presence or absence of an electrical signal generated by the transducer upon changes of said physical properties, wherein the presence and magnitude of the electrical signal is indicative of the presence and amount of an analyte in said sample.

Examples of analytes amenable to such sensor and method of detection include thiols, alcohols, amines, carbonyl compounds, carboxylic acids, amino acids, carbohydrates, sulfur oxides, aliphatic and aromatic compounds such as toluene, benzene, methane, ethane, $N_2O$, NO and $NO_2$.

As used herein, the term "redox-active protein" is meant to refer to a protein which is capable of reversibly transferring electrons. "Redox-active proteins" are capable of being reversibly reduced and oxidized. A "transducer", as used herein, is meant to refer to any means which allow the conversion of a change of a physical property of the redox active protein into an electrical signal which may be detected. Examples of a transducer are an electrode, a photometer, spectrophotometer, photomultiplier, photodiode, fluorescence microscope, fluorescence spectrophotometer, SPR spectrometer, and other spectroscopic devices, calorimeter, quartz crystal microbalance, and gravimetric devices. The term "reversibly transferring electrons" as used herein is meant to denote a process in which a redox active protein accepts or donates one or several electrons and subsequently donates accepts it/them, respectively, elsewhere, e.g. to or from a reaction partner.

The objects of the present invention are also solved by an electronic device comprising a sensor or sensor array according to the present invention. Such device is preferably selected from a computer, a mobile phone, a portable cassette player (walkman) or MP3 player, a remote control, a camera, a GPS device, or a display. The sensor or sensor array may also be integrated in items of daily use such as textiles, clothing, personal hygiene items, such as toothbrushes.

It should be noted that upon interaction of the redox active protein with a thiol analyte, the redox active protein undergoes a change in one or several physical properties. For example, it may change its absorption characteristics, or it may change its molecular weight, or it may change its redox state. Likewise, the redox active protein may also undergo a change in several physical properties at the same time, upon interaction with a thiol analyte, such as the absorption characteristics and the redox state. The transducer converts any change of physical property into an electrical signal. Depending on the type of physical property that is changed upon interaction of the redox active protein with the thiol analyte, the transducer may take on various forms, and examples of a transducer are listed above. It should therefore be noted that, in one embodiment, there may be changes in the redox state of the protein, i.e. in a sense electrical changes, which themselves are converted into an electrical signal by the transducer.

The present invention, first of all, describes a thiol detection device that is based on a specific reaction between the thiol and a protein. Thereby, the protein interacts directly with the thiol compounds by electron transfer. The altered redox state of the protein is detected as being qualitatively and quantitatively indicative for the presence of thiols. Either the polypeptide chain of the protein or a tightly bound cofactor of the protein is changed. Compared to chemical receptor materials, this invention uses redox active proteins for thiol recognition. In contrast to other protein-mediated approaches, this invention uses the direct readout of changes of the redox state of the protein in spite of employing the protein as reaction catalyst. Thereby the need for controlled use of co-reactants is circumvented. (FIG. 1). Simplicity of the readout principle is particularly interesting for gas phase analysis.

It should be noted that in accordance with the present invention, the redox active protein is not catalytically used as an enzyme in thiol conversion reactions; in one embodiment, the redox active protein does not have the in vivo physiological function in an organism to convert thiols or to catalyze such thiol conversion. In the present invention, the presence of co-reactants, other than the redox active protein itself or a cofactor or prosthetic group associated with said redox active protein, participating in such thiol conversion reactions is not necessary, in view of the fact that the redox active protein does not have the in vivo physiological function of participating in a thiol conversion reaction.

Surprisingly, proteins that do not convert thiols as their in vivo physiological function can be used in the device. E.g. cytochrome c is known as protein that shuffles electrons between two transmembrane protein complexes. An enzymatic function, in terms of converting metabolites, e.g. thiols is not known for cytochrome c.

However, in the approach according to the present invention, a protein can simply be regarded as one partner of a redox reaction comprising protein and thiol. Then one would have to assume other redox pairs being relevant as well, e.g. between protein and oxygen. Oxidation of the protein by oxygen should extinguish the signal generated by the reduction by thiols. Surprisingly, signal extinction by oxygen has not been observed by the present inventors.

It should be noted that the sensor in accordance with the present invention also enables the selective detection of thiol analytes in complex mixtures, i.e. mixtures which, in addition to thiols, also contain other chemicals, such as amines, alcohols or water.

Examples for redox active proteins are:
Metalloproteins containing heme-bound iron, like cytochrome c, horseradish peroxidase, myoglobin, hemoglobin, catalase, microperoxidase
Metalloproteins containing non-heme iron, like ferredoxin
Metalloproteins containing copper, like superoxide dismutase
Proteins containing organic cofactor like FAD (flavin adenine dinucleotide), e.g. sulfhydryl oxidase, monoamine oxidase, or FMN (flavin mononucleotide), e.g. flavin-containing monooxygenase, or NAD(P) (nicotinamide adenine dinucleotide (phosphate))
Redox active proteins that are naturally found in a lipid bilayer (membrane proteins) such as cytochrome c oxidase
All kind of derivatives of these proteins, such as chemical modifications or mutations It should be noted that the term "redox active protein" also includes derivatives of the afore-mentioned proteins. Such derivatives may be chemically modified proteins in which other compounds, such as for example sugars, lipids etc., or specific chemical functionalities have been added to the protein. Examples of such chemical modifications are outlined in "proteins" by Thomas E. Creighton, Freeman, 1993 and are well-known to someone skilled in the art. Likewise, the derivatives of the afore-mentioned proteins may include mutations, wherein amino acid residues of the amino acid sequence of the proteins have been deleted, changed or additional amino acids have been inserted or attached, respectively. Preferably, such mutations are at least 70%, preferably at least 80%, more preferably at least 90%, even more preferably at least 95% and most preferably at least 99% identical to the original sequence of the redox active protein.

In accordance with one embodiment of the present invention, the redox-active protein can be part of a transducer material containing the redox-active protein.

This transducer material can be made of:
Conducting materials like metals such as gold or alloys
Semi-conducting materials like metal oxides such as tin oxide
Materials made of carbon such as graphite or carbon nanotubes
Conducting polymers
Composite materials like organically interlinked metal nanoparticles This transducer material can be prepared by any technique, like:
Layer-by-layer assembly (dipping, flow-cell, coating)
Coating (e.g. spin-, dip-, drop- or spray coating)
Chemical or physical vapor deposition Sintering
Self-assembly
Printing (e.g. ink-jet printing, screen printing)
Stamping
Immersing In one embodiment, the redox-active protein is present in or as a layer, e.g. the aforementioned first layer, within the sensor according to the present invention. Likewise, it may also be present as a spot or a plurality of spots within the sensor. Such layer and spots are applied on a surface on or in the sensor, preferably on a surface of the transducer.

In one embodiment, the thiol analytes can be:
short- or long chain aliphatic thiols, e.g. $C_1$-$C_{20}$ thiols,
aromatic thiols
sidechains of polypeptides, like glutathione
sidechains of amino acids like cysteine
thiols dissolved in a solvent
volatile thiols in the gas phase The selectivity between thiols and non-thiols is based on a favorable electron-transfer between the protein and the thiol compound.

The selectivity between different thiols is based on a different thiol reactivity due to
steric hindrance
pK-value of the thiol group
electronic properties of non-thiol functionalities of the thiol compound.

In one embodiment, the changes of the redox-state of the protein can be followed by any suitable technique and transduction principle:
Conductivity/Resistivity
Current (amperometric by direct electron transfer)
Potential (potentiometric)
Capacity
Color changes, light absorbance or transmittance
Reflectivity
Refractive index changes
Fluorescence or phosphorescence
Luminescence
Heat (calorimetric)
Conformational changes
Changes of physiological activity
Gravimetry.

It should be noted that, usually, a further specification of the geometry of the sensing material is not necessary. In one embodiment, the sensor geometry can be of:
Flat surface of any shape
Rough surface
Porous material, like assembly of rods, spheres, or a sponge-like structure
A single layer of sensing material
Multiple layers containing protective or electrolyte layers besides the sensing material.

Embodiments of the sensor in accordance with the present invention can be used for applications like:
Medical applications to examine physical conditions or disorders. Sources of indicative volatile compounds can be breath, saliva, blood, urine, plasma, cerebrospinal fluids or pus. For instance, breath analysis or headspace analysis of physiological samples to detect halitosis, cancer or bacterial infections. Presence or absence of specific marker compounds can point to certain physiological conditions, chemical exposures or disorders like halitosis. Medical applications for monitoring of drug metabolism. Stationary and mobile applications.
In food-related applications to analyze food freshness
In agricultural testing applications
In security-related applications to detect thiol containing explosives, toxins or other harmful thiols
Environmental monitoring (e.g. waters, waste water, air)
In occupational medicine applications to monitor exposition to thiols A "redox-active protein" is a protein which is capable of reversibly transferring electrons. "Redox-active proteins" are capable of being reversibly reduced and oxidized. Immobilization of a redox-active protein on a surface, such as an electrode surface, can be achieved by a variety of means known to someone skilled in the art. Immobilization preferably occurs via chemisorption (i.e. through covalent linkages) or physisorption (i.e. through non-covalent linkages). A covalent linkage can be achieved by the protein having functional groups that are capable of reacting with other chemical functionalities to form a covalent linkage. The application of a redox-active protein to an electrode surface may occur by a variety of processes, such as simple exposure of the surface to said protein, dipping the surface into a protein solution, spin coating, spray coating, doctor blading, Langmuir-Blodgett techniques and the like. In one embodiment, the electrode is made of a material selected from metals, such as gold, alloys, metal oxides, such as tin oxide, including fluoride-doped tin oxide (FTO), carbon, such as graphite or carbon nanotubes, electrically conducting polymers, such as polyaniline, or composite material such as organically interlinked metal nanoparticle films.

Analytes to which the sensors and sensor arrays according to the present invention may be adapted, herein also sometimes referred to as "redox inactive analytes" are selected from thiols, but also (see below) alcohols, amines, carbonyl compounds, carboxylic acids, amino acids, carbohydrates, sulfur oxides, such as $SO_2$, aliphatic and aromatic compounds, such as toluene, benzene, methane, ethene, nitrous oxide ($N_2O$), nitric oxide (NO), nitrogen oxide ($NO_2$). Examples of thiol analytes are selected from the group comprising C1-C20 aliphatic thiols, aromatic thiols, side chains of amino acids, such as cysteine, side chains of polypeptides having a thiol group, such as glutathione, thiol compounds dissolved in a solvent and volatile thiols in the gas phase. Sometimes, the sample to be analyzed contains, in addition to one or several of the aforementioned analytes, also other chemicals, such as aldehydes, ketones, hydrocarbons, halogenated hydrocarbons, or water or mixtures thereof. The sample in accordance with the present invention may be gaseous, liquid or solid.

A "transducer", as used herein, is meant to refer to any means which allow the conversion of a change of physical property of the redox-active protein into an electrical signal which may be detected. Examples of a transducer are an electrode, a photometer, spectrophotometer, photomultiplier, photodiode, fluorescent microscope, fluorescent spectrophotometer, SPR spectrometer (SPR=Surface plasmon resonance) and other spectroscopic devices, calorimeter, quartz crystal microbalance and gravimetric devices. The term "reversibly transferring electrons" as used herein is meant to denote a process in which a redox-active protein accepts one or several electrons and subsequently donates it/them elsewhere, e.g. to a reaction partner or in which the redox-active protein donates one or several electrons and subsequently accepts it/them elsewhere.

The present inventors have also found that it is possible to use a basic sensor including a redox active protein and a transducer, as defined further above and as for example also described in European Patent Application 08 017 510, as a sensor platform which can be adapted to a variety of analytes and which is no longer adapted to thiols only. Whereas the sensor platform, as described in European Patent Application 08 017 510 was specific to thiol analytes, the sensors in accordance with the present invention are capable of detecting a broader range of analytes. This is achieved through the use of a coating layer which covers the aforementioned basic platform sensor and comprises an enzyme that is capable of converting a redox-inactive analyte into a redox-active compound. The redox-active compound subsequently interacts with the redox-active protein present in the platform sensor and thus leads to a change in a physical property of the redox-active protein which is subsequently converted into an electrical signal. Because the basic sensor is identical, irrespective of which analyte is to be detected, whereas the analyte specificity/versatility is achieved by the coating layer comprising an enzyme specific for said analyte, the resulting sensor is very versatile and uses operating conditions that are the same for different analytes. Hence, the sensor platform produces the same output signal irrespective of the type of analyte detected. The coating layer comprising the enzyme affords the required specificity and can be changed easily to adapt the sensor to different analytes. As used herein, the term "redox-inactive analyte", is meant to refer to compounds which do not readily react with the redox-active protein if a coating layer is present. A redox-inactive analyte is not an oxidizing agent or a reducing agent. In preferred embodiments according to the present invention, a redox-inactive analyte is an analyte selected from thiols, alcohols, amines, carbonyl compounds, carboxylic acids, amino acids, carbohydrates, sulfur oxides, aliphatic and aromatic compounds, such as toluene, benzene, methane, ethane, nitrous oxide ($N_2O$), nitric oxide (NO), and nitrogen oxide ($NO_2$).

A "redox-active compound", as used herein, is meant to refer to a compound, such as hydrogen peroxide, redox-couple NADH and NAD.

In accordance with embodiments of the present invention, the coating layer is preferably made of a polymeric material which can be easily handled, for example removed or applied to a surface, such as an electrode surface of the sensor platform. Preferably, the coating layer is made of a polymeric material. Such polymeric materials may be used in their polymeric state or in a precursor state which is subsequently induced to polymerize. There may also be crosslinking of the polymeric material involved upon formation of the coating layer. In one embodiment, the polymeric material is selected from polysaccharides, polypeptides, and non-polysaccharidic, non-polypeptidic polymers.

Typical examples of polysaccharides are starch, gummi arabicum, agarose, chitosan, alginate. Typical examples of polypeptides are poly-lysine, gelatine, self-assembling peptides, such as Fmoc-diphenylalanine, amphiphilic peptides, self-complementary ionic peptides, polymeric beta peptides, amyloidic peptides.

Non-polysaccharidic, non-polypeptidic polymers, as used herein, are for example polyacrylamides, polyacrylates, polyamides, polyesters, polycarbonates, polyamines, polyoxides, polysulfones, polystyrenes, polyethers, and polyimines.

It is possible to change specificity from one analyte to another by exchanging the coating layer comprising one enzyme against another coating layer comprising another enzyme (see FIG. 14). In accordance with the present invention, the coating layer can be removed from the sensor platform and/or exchanged against another coating layer containing a different enzyme. Accordingly, the sensor platform comprising the redox-active protein and a transducer is compatible with such a coating layer which comprises an enzymatic activity specific for a specific analyte. Whereas the sensor platform in accordance with the present invention and as described in previous European Patent Application 08 017 510 is sensitive towards thiol analytes, the use of a coating layer comprising an enzyme on top of the sensor platform (comprising a redox-active protein and a transducer), opens up a broader range of analytes to be detected by the sensor in accordance with the present invention. One would have expected that such a sensor having the sensor platform and the aforementioned coating layer on top might respond to the specific analyte (through the coating layer plus enzyme) as well as to thiols (through the sensor platform). However, contrary to this expectation, the coating layer appears to act as a kind of filter rendering the sensor almost completely insensitive for thiols (see also FIG. 14). Consequently, as soon as the specificity/selectivity of the sensor is changed from thiols to another type of analyte by using a coating layer comprising a specific enzyme, the sensor becomes insensitive to thiols. The coating layer in many embodiments has a high water content which provides an environment similar to the physiological environment for enzymes. Such coating layer seems to be a strong barrier for thiols preventing thiols from entering the active sensor surface. Sensitivity for thiols may still be achieved, though, through the use of a thiol specific enzyme in the coating layer. Analytes other than thiols, such as alcohols, amines, etc. appear to dissolve well in the coating layer or appear to be at least converted within the coating layer. Where the polymeric material used for the coating layer also contains water, this may be advantageous, when water-soluble compounds are used by the reaction of the enzyme in the coating layer with the analyte. This is particularly advantageous, if the analyte itself is water insoluble or hardly water-soluble, such as toluene and benzene. The use of such coating layer is also advantageous for gaseous samples containing volatile analytes which are enzymatically converted in the coating layer into less volatile compounds.

In addition to the increase in versatility, the use of a coating layer may also have advantageous effects in that the coating layer has preconcentrating properties by enriching the analyte in the coating material. Likewise, because the coating layer covers the sensor platform, it modulates the absolute signal intensity by reducing or enhancing the sensor surface accessibility. In those instances where the coating layer comprises a polymeric material containing water, such coating layer acts also as a water reservoir and provides for a stable environment for biomolecules in affording a long-term stability. If desired, the coating layer may also be rendered electrically conductive and may provide for chromatographic properties for an analyte pre-separation.

The sensors in accordance with the present invention can be used for medical applications to examine physical conditions or disorders by analyzing samples with complex chemical composition. Sources of indicative volatile compounds can be breath, blood, urine, plasma, saliva, cerebrospinal fluids or pus. For example, using a sensor in accordance with the present invention may provide for a breath analysis or headspace analysis of physiological samples to detect halitosis, cancer or bacterial infections. The presence or absence of specific marker compounds in such samples can point to certain physiological conditions, chemical exposures or disorders, such as halitosis. Likewise, the sensors in accordance with the present invention may also be used for monitoring drug metabolism or the progress of a drug therapy. Furthermore, the sensors may also be used in food-related applications to analyze quality and freshness of food. Moreover, they can be used in security-related applications to detect explosives, toxins or other harmful analytes. Moreover, sensors in accordance with the present invention may be used for environmental monitoring, such as water, waste water, air, and in occupational medical applications, for example to monitor exposure to analytes and maximum allowable concentrations of noxious agents.

The sensors in accordance with the present invention can be quickly adapted to a given analyte by applying the desired coating layer comprising the desired enzyme onto the aforementioned sensor platform. These modifications can be done quickly and without efforts, because the overall sensor components remain unchanged. Likewise, the signal readout and the operating parameters are kept thus simplifying the device and the instruments. This makes operation by laypersons possible. Likewise, the production of sensor devices in accordance with the present invention is cheap, since parts of the device can be used universally in different sensor applications. Moreover, it also possible to provide for sensor arrays with only one readout mechanism which, in turn, allows a scanning of a large number of samples in a swift manner. Furthermore, the exchangeability of coating layers facilitates sensor measurements of an analyte in different aggregate states. For example, there is a combination of enzyme and redox active protein that is able to sense an alcohol analyte. Imagine that there is a best sensor architecture to measure alcohol gas in a vapor sample and a best way to measure alcohol dissolved in water. If the difference between both architectures is implemented in the coating layer then one can adapt the sensor quickly to the different states of alcohol by changing the coating layer. Alternating measurements in solution and in gaseous phase are possible with one single device due to the additional protective properties of the coating layer employed. Furthermore, the exchangeability of the coating layer facilitates the regeneration of sensor if the coating layer got contaminated or if cross-contamination of different samples has to be avoided or if hygienic requirements demand renewal of the sample-sensor-interface.

It should be noted that upon interaction of the redox-active protein in the sensor platform, as described in European patent application No. 08 017 510, with an analyte, or if a coating layer is present containing an enzyme, with the redox-active compound produced by the enzymatic reaction of the enzyme with an analyte, the redox-active protein undergoes a change in one or several physical properties. For example, it may change its absorption characteristics, or it may change its molecular weight, or it may change its redox state. Likewise, the redox-active protein may also undergo a change in several physical properties at the same time upon interaction with a redox-active compound produced by the enzymatic reaction of the enzyme in the coating layer with an analyte. For example, both the absorption characteristics and the redox state may change. The transducer converts any change of physical property into an electrical signal. Depending on the type of physical property that is changed upon interaction of the redox-active protein with the redox-active compound, the transducer may take on various forms, and examples of a transducer are listed above. It should therefore be noted that, in one embodiment, there may be changes in the redox state of the protein, i.e. in a sense an electrical change, which itself is subsequently converted into an electrical signal by the transducer.

The basic sensor platform, as described in European patent application No. 08 017 510.2 is based on a specific reaction between a redox-active analyte, for example a thiol. Thereby, the protein interacts directly with the redox-active analyte by electron transfer. The altered redox state of the protein is detected as being qualitatively and quantitatively indicative for the presence of an analyte. Either the polypeptide chain of the protein or a tightly bound cofactor of the protein is changed. Compared to chemical receptor materials, this invention uses redox-active proteins for analyte recognition. In contrast to other protein-mediated approaches, this invention uses the direct readout of changes of the redox state of the protein in spite of employing the protein as a reaction catalyst. Thereby, the need for controlled use of co-reactants is circumvented. A simplicity of the readout principle is particularly interesting for a gas phase analysis.

As used herein, a "redox-inactive analyte" is a chemical substance that is of analytical interest which means that either presence of that compound or quantity of that compound or both is unknown and needs to be determined. This chemical substance, however, is redox-inactive, which means that the substance is not able to react directly under experimental conditions with the redox-active protein which itself is preferably immobilized on an electrode. The experimental conditions comprise the architecture of the sensor (e.g. protective coating layer on top of the redox-active protein) and parameters of operating the sensor (e.g. applied voltage to the electrode, operating temperature) and timeframe within which the analytical result needs to be obtained. Examples of redox-inactive analytes have been listed further above.

As used herein, a "redox-active compound" is a chemical substance that is not of direct analytical interest. Presence of this substance or its quantity or both is only of interest in order to determine presence or quantity or both of a "redox-inactive analyte". The "redox-active compound" originates from a reaction in which "redox inactive analyte" was involved. The "redox-active compound" can be a derivate of the "redox-inactive analyte" or a derivate of a third compound that also participated in the reaction. In contrast to "redox inactive analyte", the "redox-active compound" is able to react directly under experimental conditions with the redox-active protein which itself is preferably immobilized on an electrode. The experimental conditions comprise the architecture of the sensor (e.g. protective coating layer on top of the redox-active protein) and parameters of operating the sensor (e.g. applied voltage to the electrode, operating temperature) and timeframe within which the analytical result needs to be obtained. Examples of redox-active compounds have been listed further above.

As used herein, a "redox-active analyte" is a chemical substance that is of analytical interest which means that either presence of that compound or quantity of that compound or both is unknown and needs to be determined. This chemical substance is redox-active, which means that the substance is able to react directly under experimental conditions with the redox-active protein which itself is preferably immobilized on an electrode. The experimental conditions comprise the architecture of the sensor (e.g. protective coating layer on top of the redox-active protein) and parameters of operating the sensor (e.g. applied voltage to the electrode, operating temperature) and timeframe within which the analytical result needs to be obtained.

In the following, reference is made to the figures wherein

FIG. 1 shows a sensor principle in accordance with the present invention, wherein the thiol analyte interacts directly with the redox-active protein by electron transfer. Changes in the redox state are probed directly either by optical detection or by means of an electrode on which said redox-active protein is immobilized and finally transduced to an electrical signal.

FIG. 2 shows cytochrome c immobilized on mesoporous $SnO_2$ by electrostatic interactions. $SnO_2$ functions as electrode. The intimate contact between the protein and the electrode allows electron transfer to occur. Thiols react with oxidized cytochrome c by transferring an electron and reducing cytochrome c thereby. Light is characteristically absorbed by the protein.

FIG. 3 shows the absorption spectrum of Fe(III) state and Fe(II) state cytochrome c which show characteristic differences. The transition between fully oxidized and reduced cytochrome c can be observed. The reduction can be induced by thiols or electrochemically. The inset in the upper right shows UV-Vis spectra of reduced and oxidized cytochrome c over a broader wavelength range than in the main part of the figure. The axes in the inset are the same as in the main figure. The main figure shows the part of the spectrum in more detail that is indicated in the inset by a circle.

FIG. 4 shows the relationship between DTT concentration and the intensity of spectral changes of cytochrome c. DTT is the abbreviation for dithiothreitol ($C_4H_{10}O_2S_2$). The signal is derived from spectral changes at 550 nm caused by the DTT-induced transition from cytochrome c Fe(III) state to the Fe(II) state and plotted versus the applied DTT concentration. A linear relation can be fitted to the data.

FIG. 5 shows the time dependent current of cytochrome c modified electrode before and after addition of DTT. A constant potential of +80 mV vs. Ag/AgCl was applied to the electrode. Addition of DTT leads to reduction of cytochrome c. The electrons are subsequently transferred to the electrode and can be measured by increased currents.

FIG. 6 shows intensity of anodic current versus DTT concentration measured with a cytochrome c modified electrode. The intensity of the steady state current caused by the reduction of cytochrome c by DTT and its subsequent reoxidation by the electrode is taken as signal and plotted versus the applied DTT concentration. A linear relation can be fitted to the data.

FIG. 7 shows the absorption spectrum of Fe(III) state and Fe(II) state myoglobin which show characteristic differences. The transition between oxidized and reduced myoglobin can be observed. The reduction can be induced by DTT.

FIG. 8 shows the relationship between DTT concentration and the intensity of spectral changes of myoglobin. DTT is the abbreviation for dithiothreitol ($C_4H_{10}O_2S_2$). The signal is derived from spectral changes at 500 nm caused by the DTT-induced transition from myoglobin Fe(III) state to the Fe(II) state and plotted versus the applied DTT concentration. A linear relation can be fitted to the data.

FIG. 9 shows intensity of anodic current versus DTT concentration measured with a myoglobin modified electrode. The intensity of the steady state current caused by the reduction of myoglobin by DTT and its subsequent reoxidation by the electrode is taken as signal and plotted versus the applied DTT concentration. A linear relation can be fitted to the data.

FIG. 10 shows intensity of anodic current versus DTT concentration measured with a sulfhydryl oxidase modified electrode. The intensity of the steady state current caused by the reduction of sulfhydryl oxidase by DTT and its subsequent reoxidation by the electrode is taken as signal and plotted versus the applied DTT concentration. A linear relation can be fitted to the data.

Figure 13:
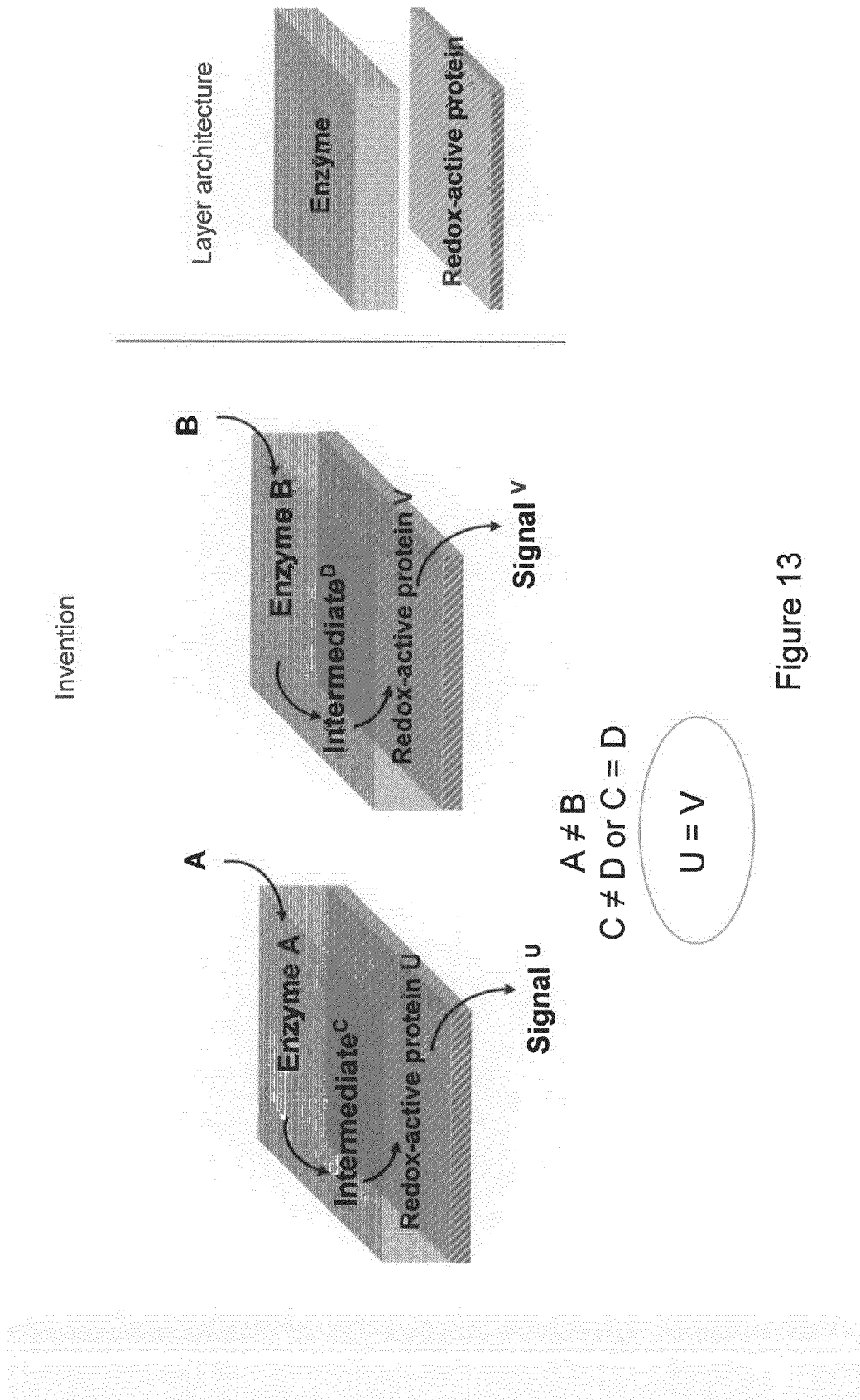

FIG. 13 shows an embodiment in accordance with the present invention, where a coating layer comprising a specific enzyme is applied on a sensor platform containing a redox-active protein and a transducer. Sensor specificity for a particular analyte is achieved through appropriate choice of the enzyme in the coating layer. The drawing on the right shows the layered architecture of the sensor. The redox-active protein is immobilized on the transducer while the enzyme is part of the coating layer.

Figure 14:
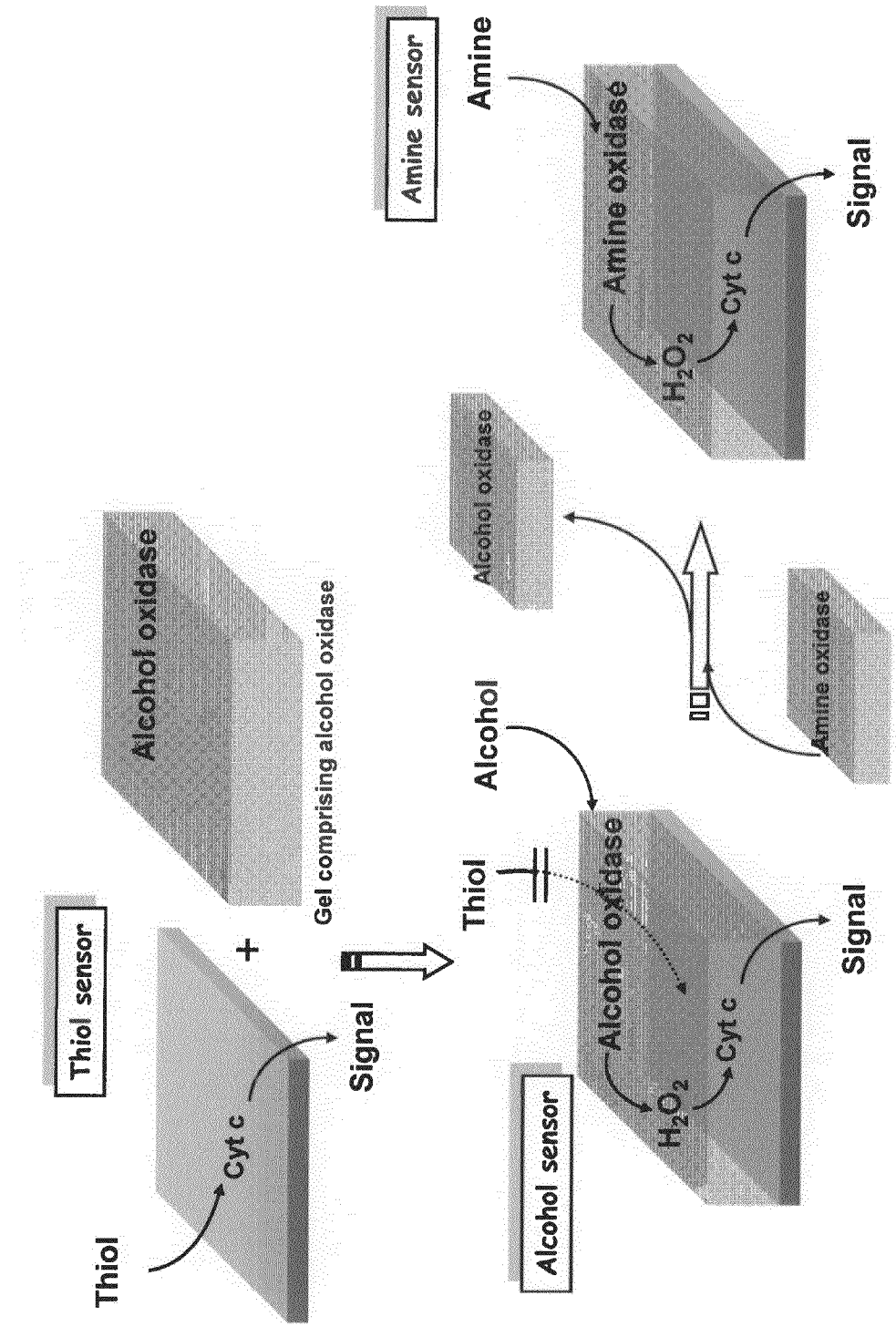

FIG. 14 shows that the coating layer, when applied to a thiol sensor as described in European patent application No. 08 017 510, acts as a filter rendering the sensor almost completely insensitive for thiols. Moreover, the specificity of the sensor is changed from thiols to another type of analyte by appropriate choice of the enzyme in the coating layer. Moreover, the specificity of the sensor is changed once more from an analyte to another type of analyte by exchanging an existing coating layer by another type of coating layer.

Figure 15:
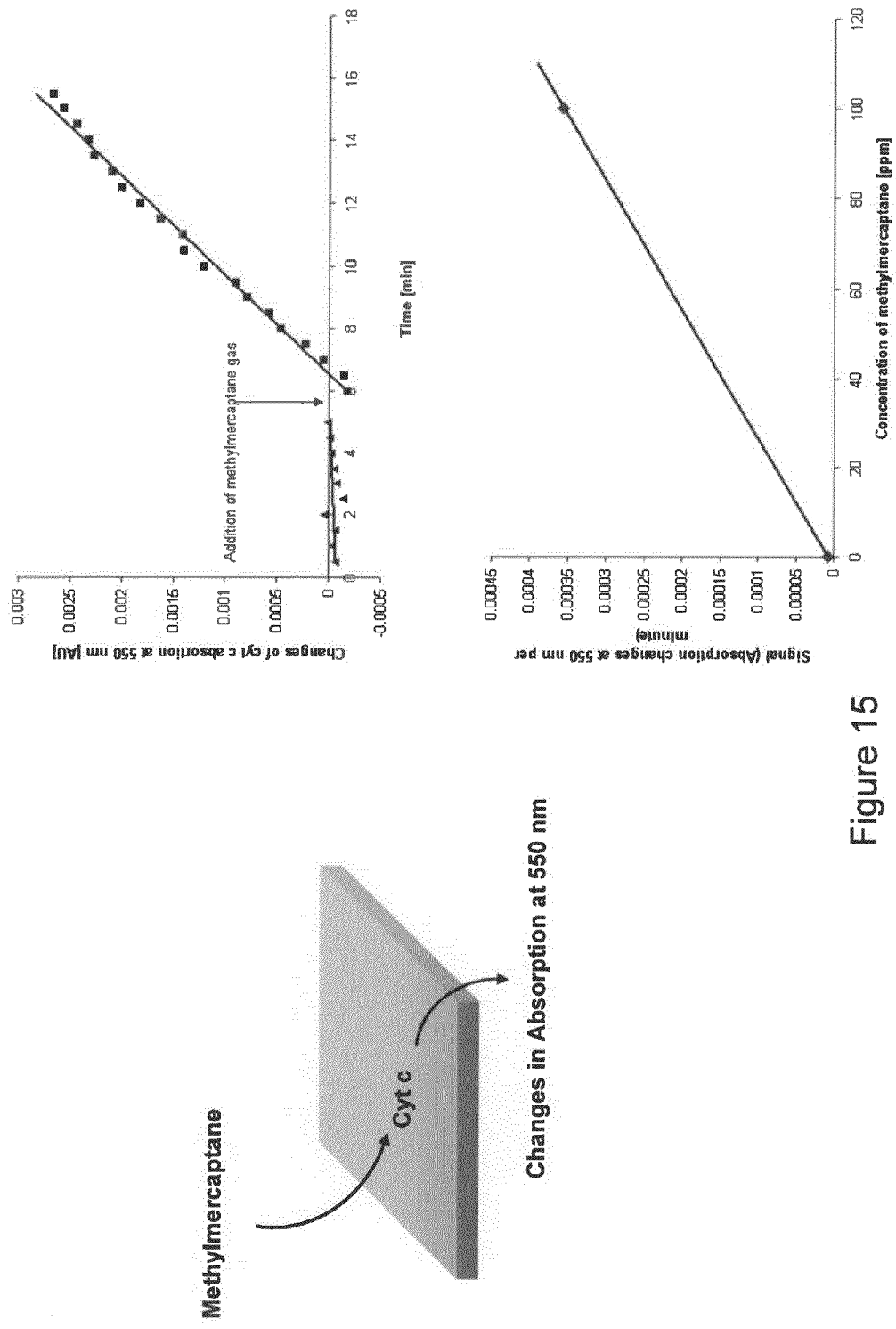

FIG. 15 shows a sensor for the detection of methylmercaptane in a gas sample. The graphs show the absorption at 550 nm of cytochrome c plotted versus time, and the sensor response, measured by absorption changes per minute at 550 nm, versus the concentration of the analyte.

Figure 16:
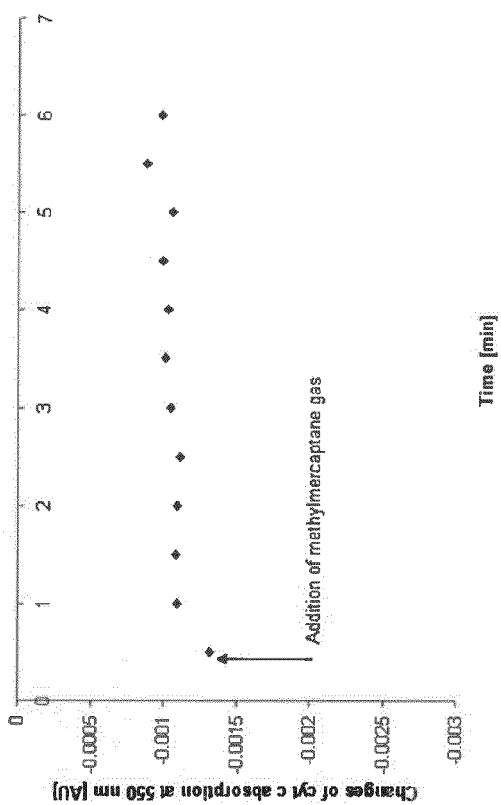
Figure 16:
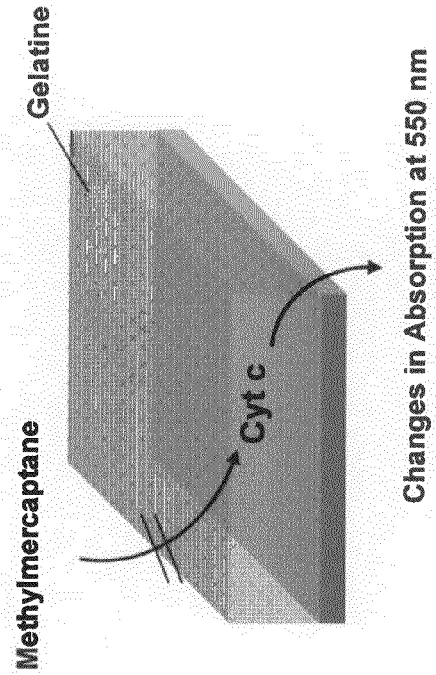

FIG. 16 shows the same sensor as FIG. 15, but additionally having gelatine (or another suitable polymeric material as described further above) as a coating layer, which thus renders the sensor insensitive to methylmercaptane in a gas sample. The graph again shows the absorption at 550 nm of cytochrome c versus time.

Figure 17:
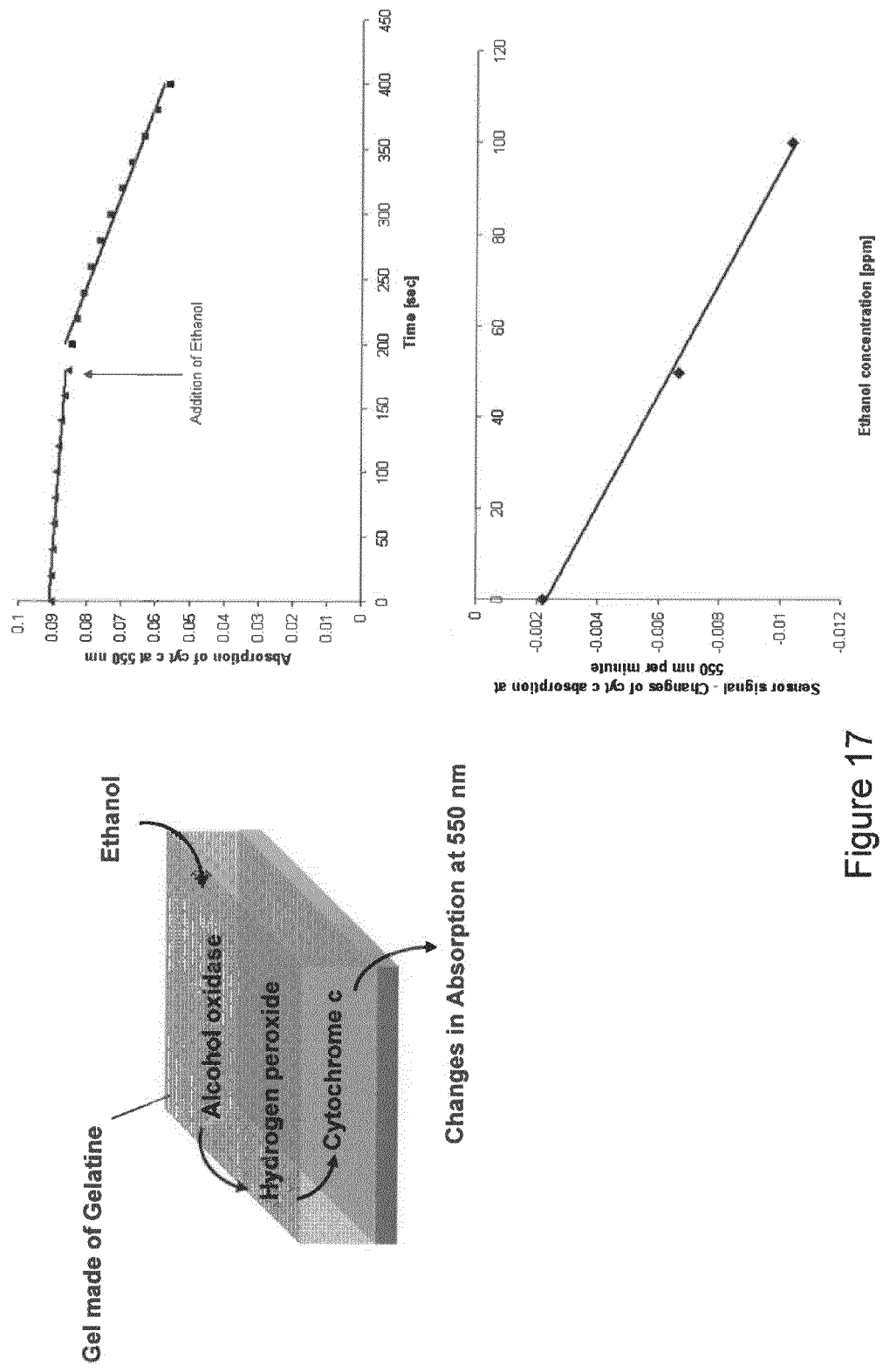

FIG. 17 shows the sensor of FIG. 16 wherein, additionally, the coating layer contains an enzyme specific for a particular analyte (alcohol oxidase for ethanol as analyte) and converting such analyte (ethanol) into a redox-active compound (hydrogen peroxide). Again, the absorption of cytochrome c at 550 nm versus time is plotted as well as the sensor signal, measured as absorption changes per minute at 550 nm versus analyte concentration.

Figure 18:
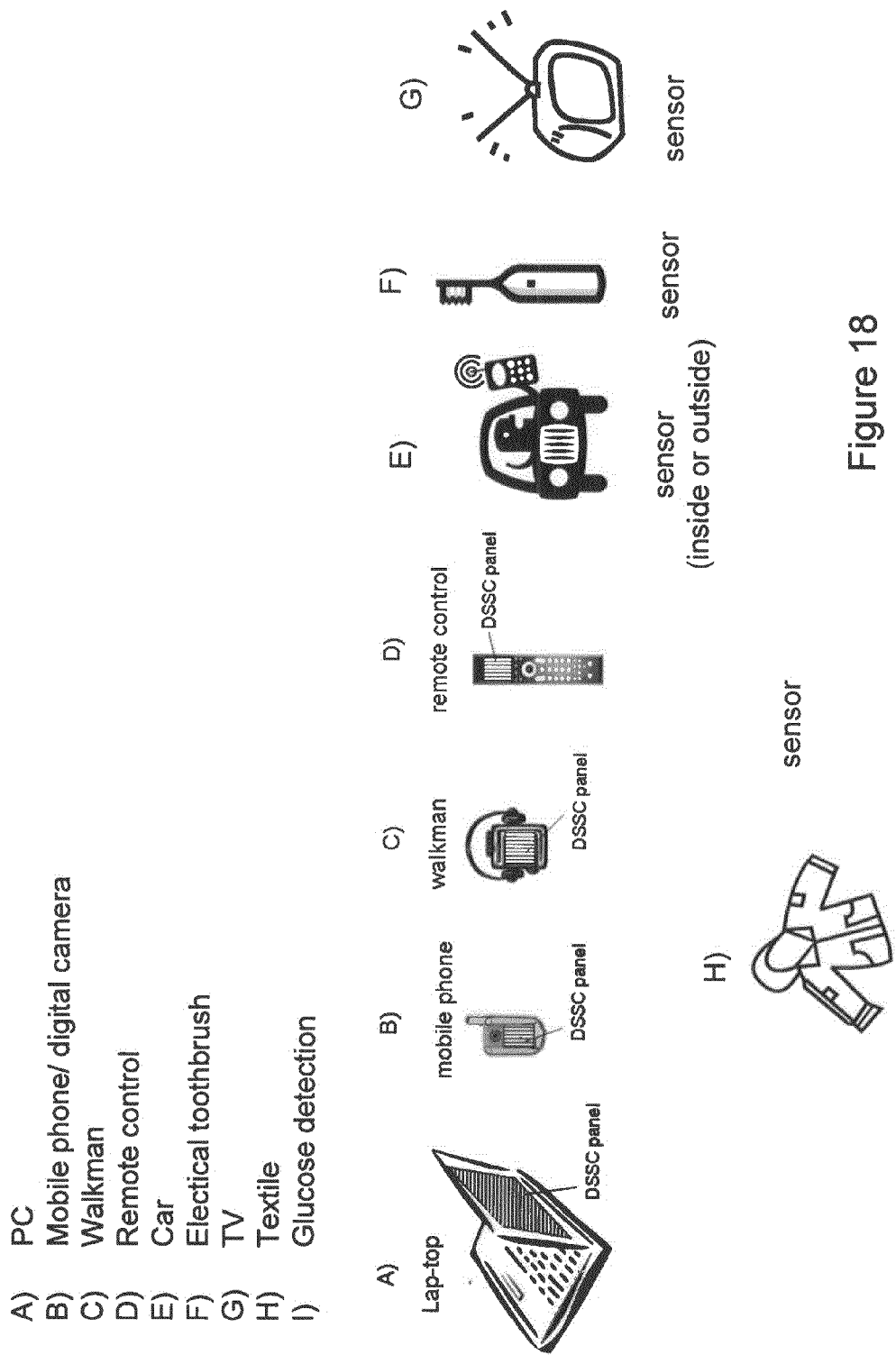
Figure 19:
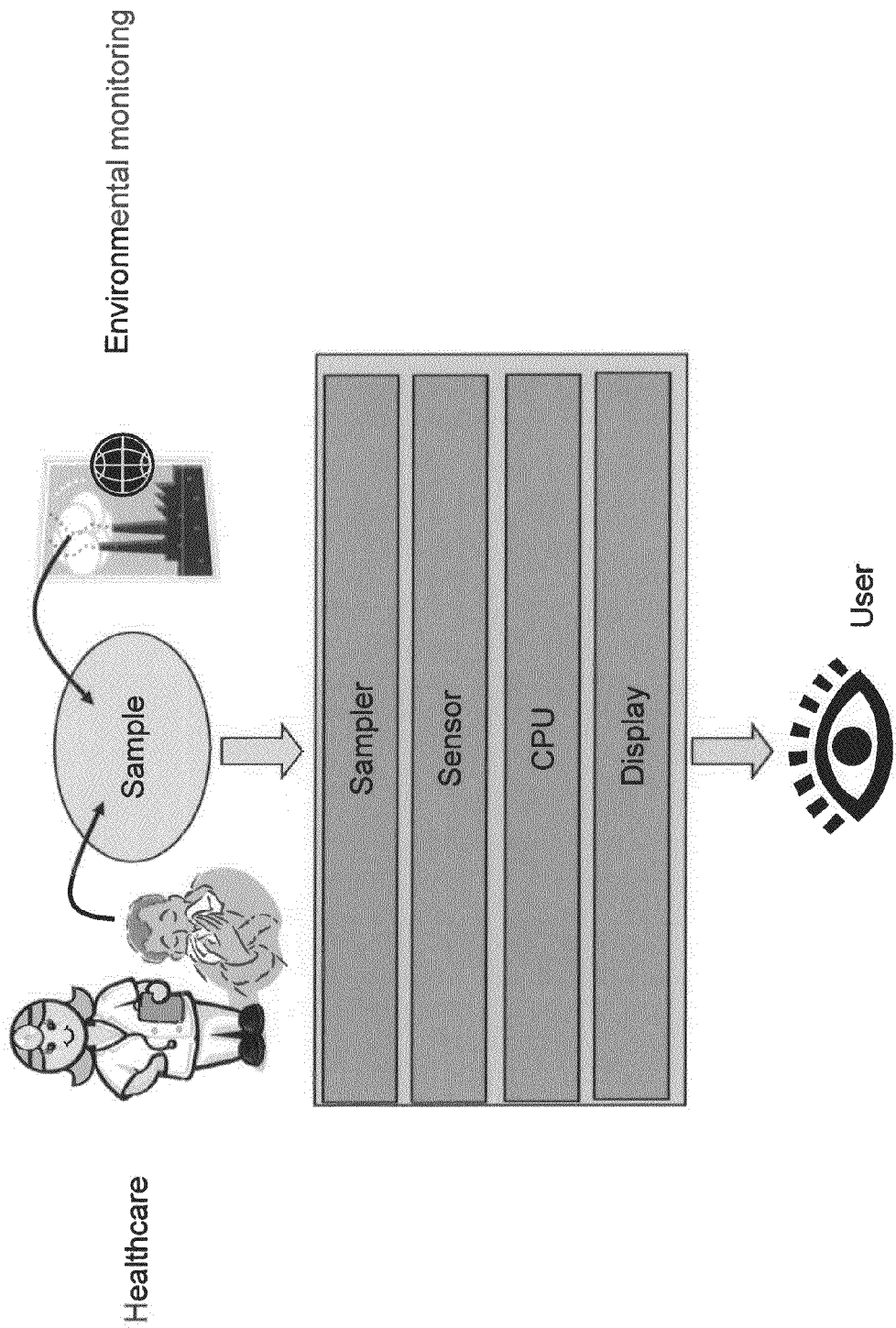

FIGS. 18 and 19 show possible devices into which the sensor according to the present invention may be incorporated, and a flow diagram of a potential use of the sensor according to the present invention in healthcare or environmental monitoring. The product comprising the present invention is made up by an electronic device comprising a sensor as defined above. The device preferably comprises a sampler, a CPU, and a display in addition to the sensor. The device can exclusively function as a sensor device. The device can also have other functions in addition to the sensor function. Therefore, examples of electronic devices comprising a sensor in accordance with the present invention include sensors, portable electronic devices and displays, such as mobile phones, notebooks, laptops, portable audio-tape players, MP3-players, remote controls, e-cards, e-books, e-readers, portable CD players, portable DVD players, cameras, digicams, GPS devices, displays integrated in electronic devices and portable sensor devices. Moreover, the device hosting the sensor in accordance with the present invention or the sensor itself can be attached to or integrated in items of daily use such as textiles or clothing items.

Moreover, reference is made to the following examples which are given to illustrate but not to limit the present invention.

EXAMPLES

Example 1

Optical Sensor with Cytochrome c on $SnO_2$ for the Detection of Dithiothreitol

Figure 1:
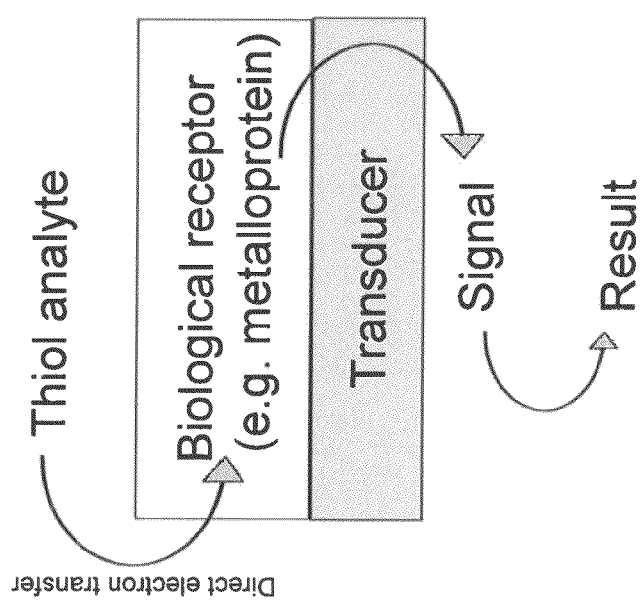
Figure 2:
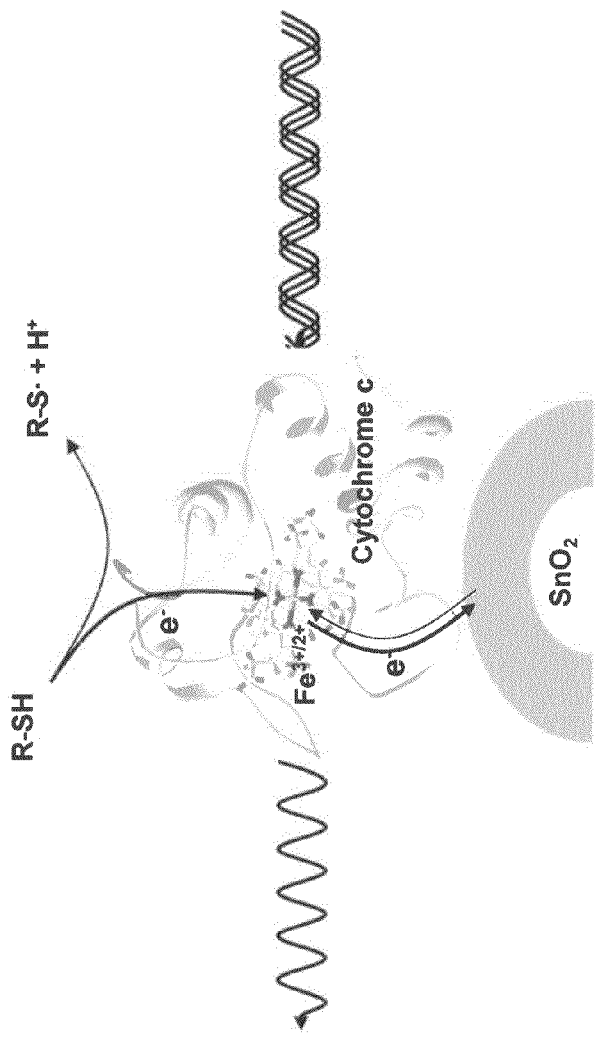
Figure 3:
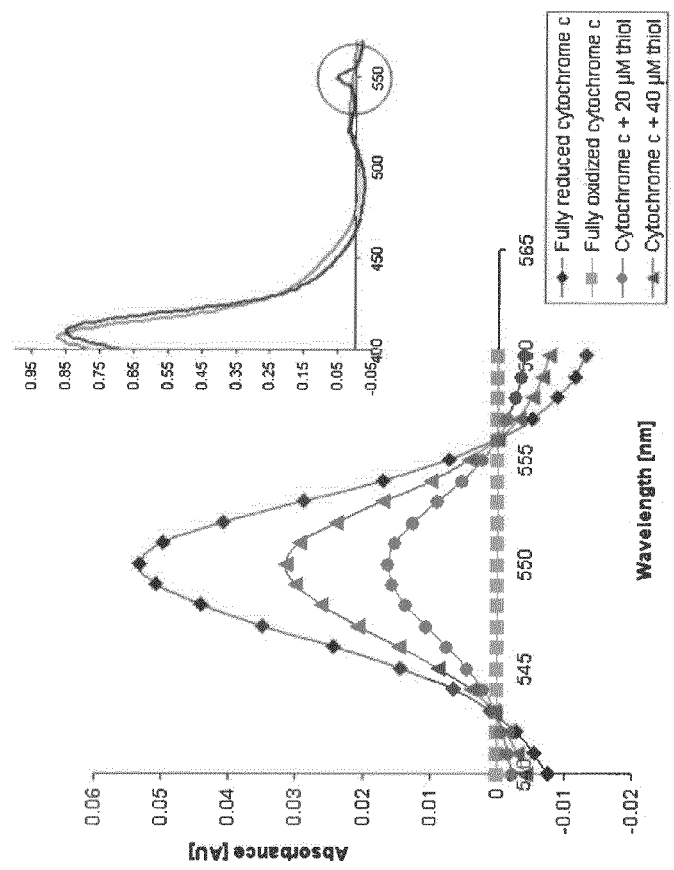
Figure 4:
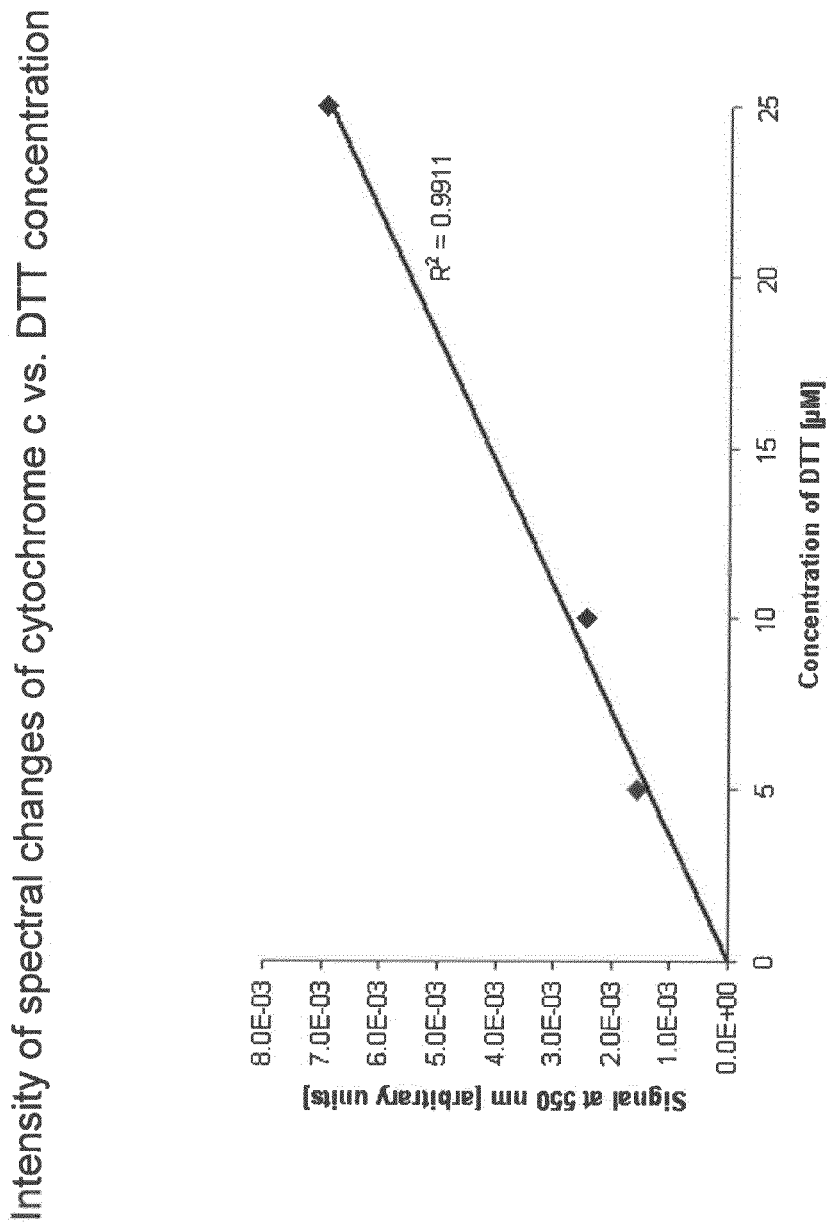

Cytochrome c was immobilized on mesoporous $SnO_2$ as transparent electrode (FIG. 2). By applying a certain potential (e.g. +200 mV vs. Ag/AgCl) cytochrome c can be set to the oxidized state (heme Fe(III)). The cytochrome c Fe(III) state shows a characteristic absorption spectrum that differs characteristically from the absorption spectrum of the Fe(II) state (FIG. 3). Bringing cytochrome c in contact with DTT (thiols) will lead to reduction of cytochrome c from Fe(III) to Fe(II) that can be observed by changes in the absorption spectrum. The intensity of spectral changes is proportional to the applied DTT concentration (FIG. 4). After calibration, the DTT concentration can be determined from the intensity of signal changes. Amines, alcohols and water do not show any influence on the redox state of cytochrome c. The sensor works reversibly and can be reset to its original state by applying potential for cytochrome c oxidation.

Example 2

Figure 5:
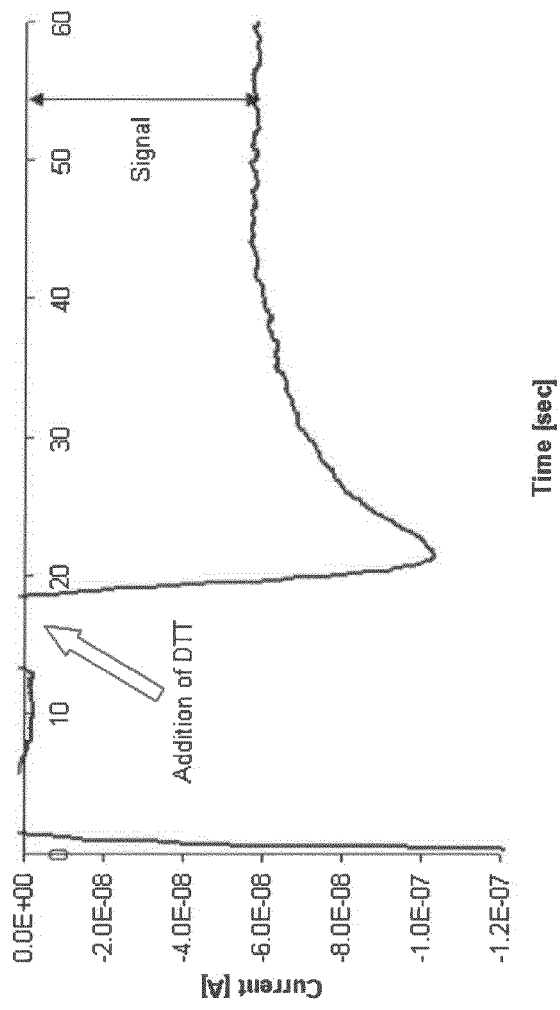
Figure 6:
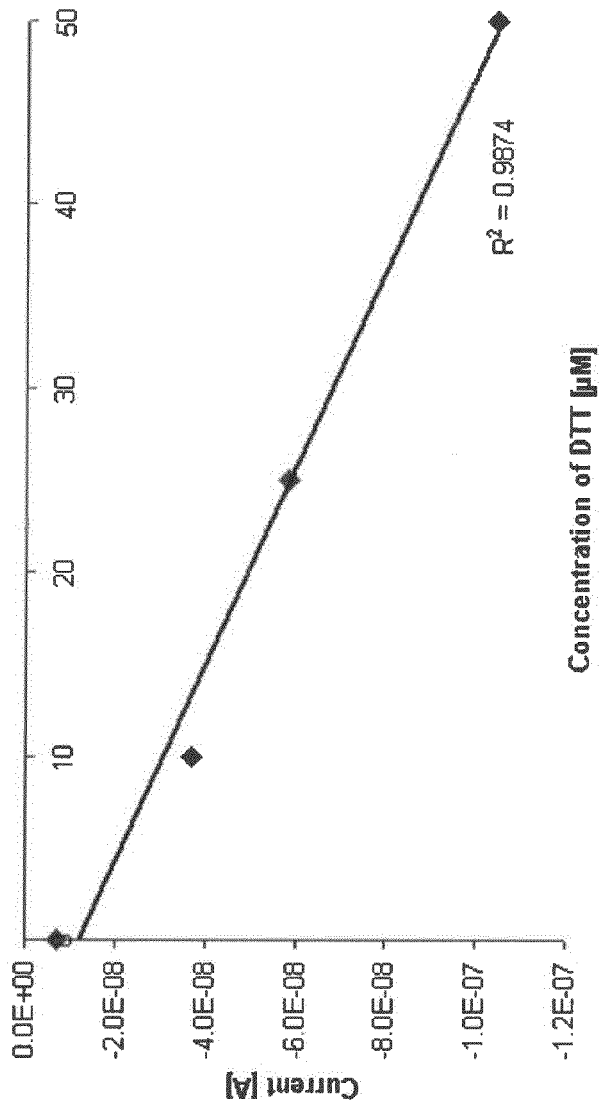

Electrochemical Sensor with Cytochrome c on $SnO_2$ for the Detection of Dithiothreitol Cytochrome c was immobilized on mesoporous $SnO_2$ as transparent electrode (FIG. 2). A defined proportion of oxidized (Fe(III)) and reduced (Fe(II)) cytochrome c can be set by applying a defined potential, e.g. +80 mV vs. Ag/AgCl. Bringing cytochrome c in contact with DTT (thiols) will lead to reduction of cytochrome c from Fe(III) to Fe(II). Since the potential dictates the ratio between Fe(III) and Fe(II), electrons transferred from DTT to Fe(III) can be observed in an increased anodic current (FIG. 5). The intensity of the anodic current is proportional to the applied DTT concentration (FIG. 6). After calibration, the DTT concentration can be determined from the intensity of anodic current. Amines, alcohols and water don't show any influence on the redox state of cytochrome c. The sensor works reversibly.

Example 3

Figure 7:
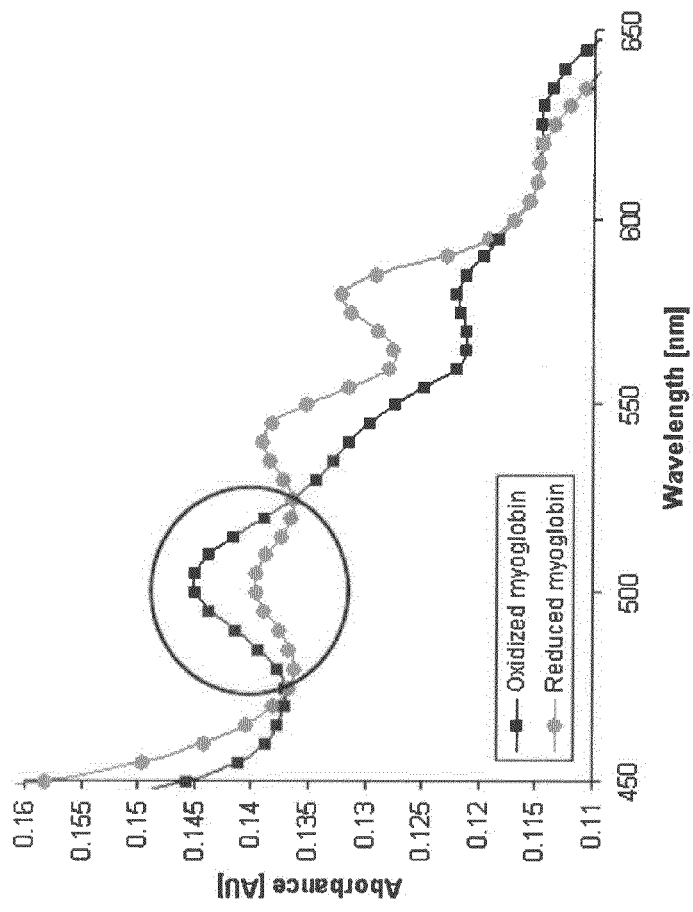
Figure 8:
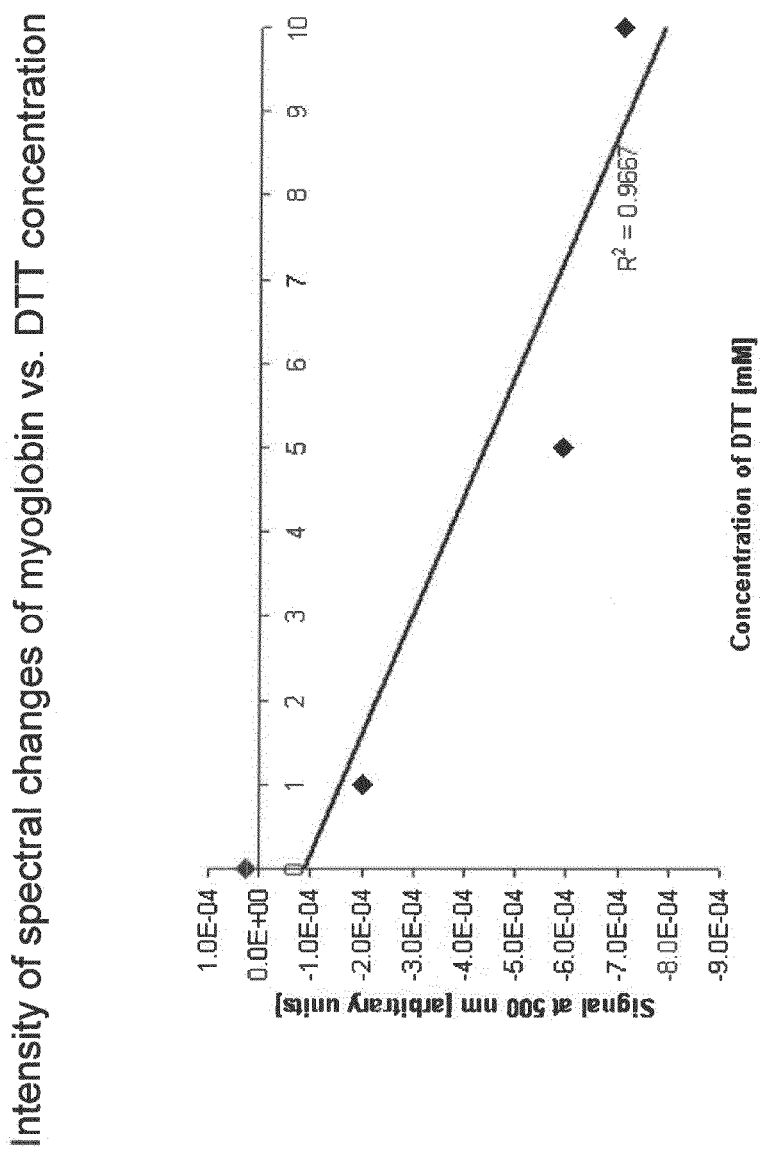
Figure 9:
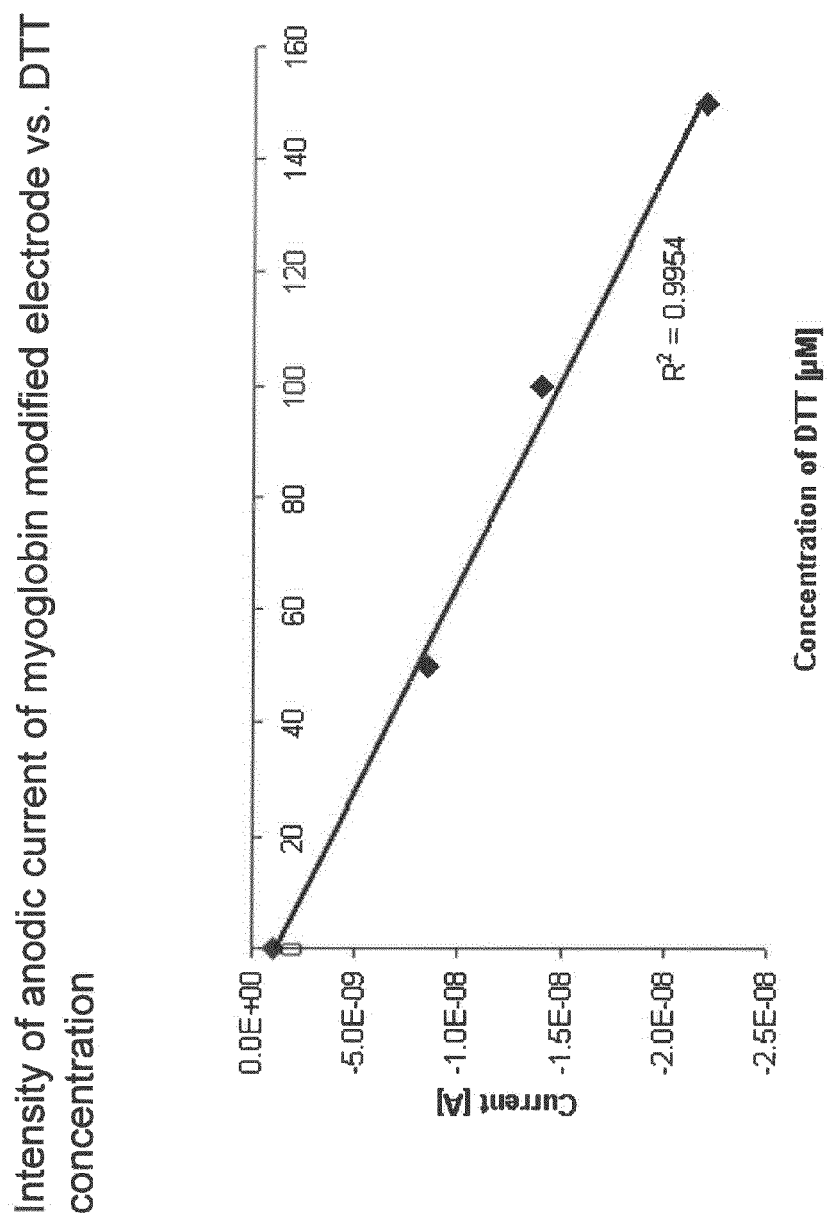

Electrochemical Sensor with Myoglobin on $SnO_2$ for the Detection of Dithiothreitol Myoglobin was immobilized on mesoporous $SnO_2$ as transparent electrode (analogous to FIG. 2). A defined proportion of oxidized (Fe(III)) and reduced (Fe(II)) cytochrome c can be set by applying a defined potential, e.g. +80 mV vs. Ag/AgCl. Bringing myoglobin in contact with DTT (thiols) will lead to reduction of myoglobin from Fe(III) to Fe(II). This process can also be observed by spectroscopic techniques with dissolved myoglobin (FIGS. 7 and 8). Since the potential dictates the ratio between Fe(III) and Fe(II), electrons transferred from DTT to Fe(III) can be observed in an increased anodic current. The intensity of the anodic current is proportional to the applied DTT concentration (FIG. 9). After calibration, the DTT concentration can be determined from the intensity of anodic current. The sensor works reversibly.

Example 4

Figure 10:
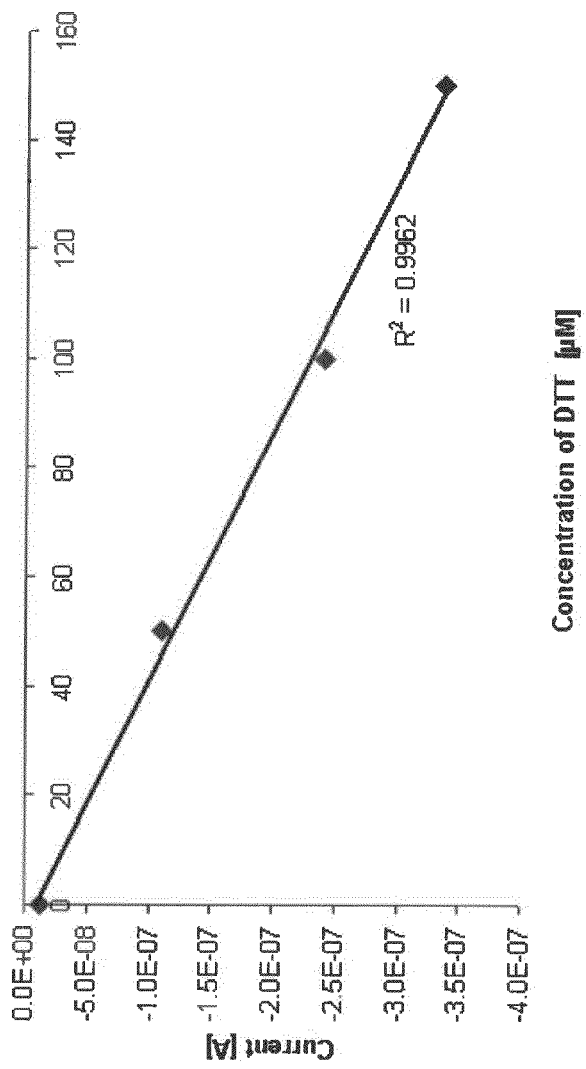
Figure 11:
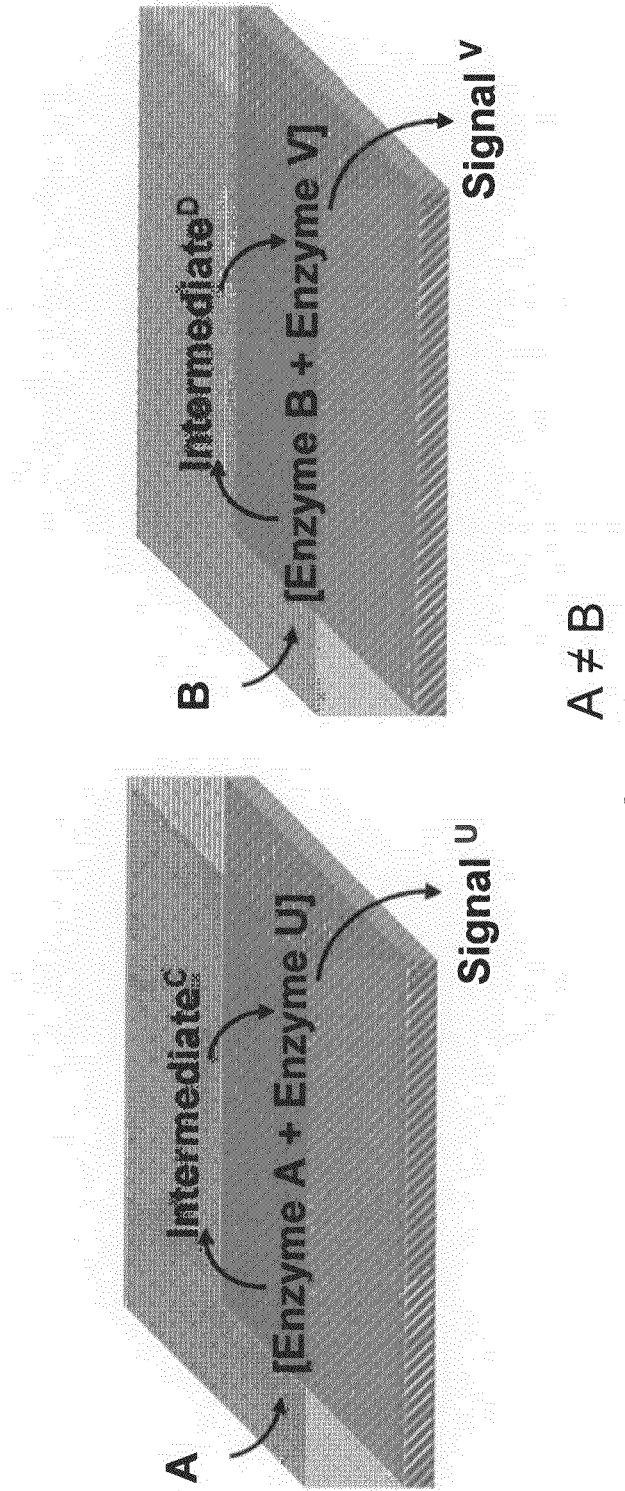
FIG. 11 shows two sensor systems for two analytes A and B in each of which the respective analyte is converted in a preceding step into an intermediate compound and is subsequently further converted by a second enzyme. The first enzyme is not directly involved in generating the measurable readout signal.
Figure 12:
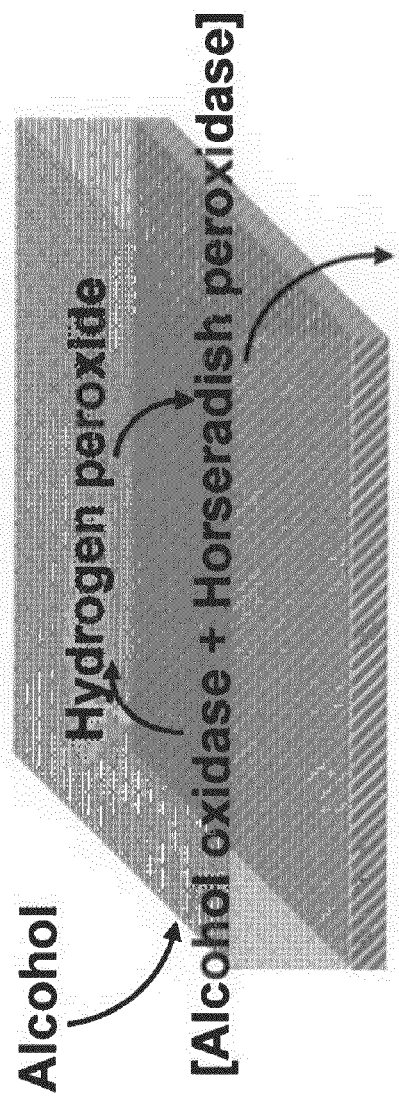
FIG. 12 shows an example for the detection of alcohol through the interplay of alcohol oxidase and horseradish peroxidase with hydrogen peroxide as intermediate.

Electrochemical Sensor with Sulfhydryl Oxidase on $SnO_2$ for the Detection of Dithiothreitol Sulfhydryl oxidase was immobilized on mesoporous $SnO_2$ as transparent electrode (analogous to FIG. 2). Bringing the protein in contact with DTT (thiols) will lead to reduction of a disulfide bridge and the electrons are subsequently relayed to the FAD cofactor and further to the electrode. The electrode is the final electron acceptor due to its applied potential and its electrical contact to the protein. This process leads to an anodic current and the intensity of the anodic current is proportional to the applied DTT concentration. After calibration, the DTT concentration can be determined from the intensity of anodic current (FIG. 10). The sensor works reversibly.

The sensor according to the present invention provides an improved specificity and thiol sensing by using a protein as a recognition element for thiol analytes. Moreover, the sensor in accordance with the present invention is capable of operating in complex sensor environments, for example in the presence of oxygen or water, since, surprisingly the presence of oxygen has no effect on the magnitude of the signal measured. Signal extinction by oxygen has not been observed in accordance with the present invention. The sensor in accordance with the present invention can be used for analytes in the gas and the liquid phase, and the simplicity of the readout (direct readout omitting the need to control the parameters of other co-reactants) is particularly interesting for a sensor device. Simplicity of the sensing allows for minaturization and reversible operation of the sensor. The sensor in accordance with the present invention provides an improved sensitivity by detecting direct changes of the protein in terms of its redox state. Moreover, the sensor in accordance with the present invention needs less reactants than devices published so far. Most published sensors rely on at least one more reaction compound such as oxygen. Many sensors are based on fluidic systems that are difficult to integrate into devices that are miniaturized, mobile, have long life-time, or are intended for multi-use applications. Moreover, the sensor in accordance with the present invention allows for a real-time analysis and can be operated without special expertise or additional hardware.

Example 5

Sensor (Cytochrome c Modified Tin Oxide on FTO-Electrode) to Detect Methylmercaptane in a Gas Sample (FIG. 15)

(Left image) Sensor architecture shows schematically cytochrome c modified tin oxide on FTO substrate. Cytochrome c directly interacts with methylmercaptane that results in increased absorption at 550 nm. The right top graph shows the absorption at 550 nm of cytochrome c plotted versus time. The moment of switching from humidified air as reference sample to 100 ppm humidified methylmercaptane gas is indicated by an arrow. The right bottom graph shows sensor response, taken as changes of cytochrome c absorption at 550 nm per minute, and plotted versus different concentrations of methylmercaptane in humidified air.

Example 6

Sensor from Example 1 with Gelatine as Top Layer that Became Insensitive to Methylmercaptane in Gas Sample (FIG. 16)

(Left image) Sensor architecture shows schematically cytochrome c modified tin oxide on FTO (fluorine-doped tin oxide) substrate. Cytochrome c is not able to interact with methylmercaptane because the interaction is prevented by a coating layer of gelatine. That is why there is constant absorption at 550 nm. The graph shows the absorption at 550 nm of cytochrome c plotted versus time. The moment of switching from humidified air as reference sample to 100 ppm humidified methylmercaptane gas is indicated by an arrow.

Example 7

Sensor from Example 2 with Addition of Alcohol Oxidase and its Response to Ethanol (FIG. 17)

(Left image) Sensor architecture shows schematically cytochrome c modified tin oxide on FTO substrate. Cytochrome c interacts with hydrogen peroxide that results in decreased absorption at 550 nm. The hydrogen peroxide is produced by a conversion of ethanol. The conversion of ethanol is catalyzed by alcohol oxidase that was embedded in the gelatin coating layer. The right top graph shows the absorption at 550 nm of cytochrome c plotted versus time. The moment of switching from humidified air as reference sample to 100 ppm humidified ethanol gas is indicated by an arrow. The right bottom graph shows sensor response, taken as changes of cytochrome c absorption at 550 nm per minute, and plotted versus different concentrations of ethanol in humidified air.

The features of the present invention disclosed in the specification, the claims and/or in the accompanying drawings, may, both separately, and in any combination thereof, be material for realizing the invention in various forms thereof.

The invention claimed is:

1. A sensor comprising:
    a redox active protein, which, upon interaction with a thiol analyte, undergoes a change in a physical property, and
    a transducer, which, upon the change in the physical property of the redox active protein, converts the change in the physical property into an electrical signal,
    wherein the redox active protein is selected from the group consisting of:
    a protein having two cysteine residues that can reversibly form a disulfide bond;
    a protein having at least one prosthetic group selected from the group consisting of flavin adenine dinucleotide (FAD), nicotinamide adenine dinucleotide (NAD), nicotinamide adenine dinucleotidephosphate (NADP), and flavin mononucleotide (FMN);
    a metalloprotein comprising copper;
    a metalloprotein comprising a non-heme iron;
    a metalloprotein comprising a heme-bound iron, selected from the group consisting of cytochrome c, myoglobin, and hemoglobin; and
    a membrane protein comprising a redox active group.

2. The sensor according to claim 1, wherein the physical property is selected from the group consisting of redox state, electrical conductivity/resistivity, current, potential, capacity, light absorbance, light transmittance, reflectivity, refractive index, fluorescence, phosphorescence, luminescence, mass as determined by gravimetry or mass-sensitive resonance techniques, heat as determined by calorimetry, conformation and physiological activity of the protein.

3. The sensor according to claim 1, wherein:
    the physical property is light absorbance, light transmittance, reflectivity, refractive index, fluorescence, phosphorescence, or luminescence;
    the transducer converts the change in the physical property into an electrical signal; and
    the transducer is a photometer or spectrophotometer or other device that measures light intensity.

4. The sensor according to claim 1, wherein:
    the physical property is a redox state of the protein;
    the transducer converts the change in the redox state into an electrical signal; and
    the transducer is an electrode upon which the redox active protein is immobilized.

5. The sensor according to claim 4, wherein the electrode comprises a material selected from the group consisting of a metal, an alloy, a metal oxide, carbon, an electrically conducting polymer, and a composite material.

6. The sensor according to claim 4, wherein the redox active protein is immobilized by chemisorption or physisorption.

7. The sensor according to claim 1, wherein the redox active protein is disposed in a first layer, in a spot, or in a plurality of spots within the sensor.

8. The sensor according to claim 7, further comprising a coating layer which covers the first layer, the spot, or the plurality of spots, wherein the coating layer comprises an enzyme.

9. The sensor according to claim 8, wherein the enzyme converts a redox inactive analyte into a redox active compound, or produces a redox active compound upon reaction with a redox inactive analyte.

10. The sensor according to claim 9, wherein the redox active compound is $H_2O_2$, and the redox inactive analyte is thiol.

11. The sensor according to claim 9, wherein the redox active protein, upon interaction with the redox active compound, undergoes a change in a physical property.

12. The sensor according to claim 7, wherein the redox active protein is immobilized in the first layer, and the first layer is disposed on an electrode or on an electrically non-conducting substrate.

13. The sensor according to claim 1, wherein the thiol analyte is selected from the group consisting of a $C_1$-$C_{20}$ aliphatic thiol, an aromatic thiol, a side chain of an amino acid, a side chain of a polypeptide having a thiol group, a thiol compound dissolved in a solvent, and a volatile thiol in a gas phase.

14. A sensor array, comprising a plurality of the sensor of claim 1.

15. A method of detecting a thiol analyte, comprising:
    exposing the sensor of claim 1 to a sample, and
    measuring a presence or an absence of an electrical signal generated by the transducer upon the change of the physical property of the redox active protein, wherein the presence and magnitude of the electrical signal indicates a presence and an amount of a thiol analyte in the sample.

16. The method according to claim 15, wherein the sample comprises a thiol analyte and at least one other chemical selected from the group consisting of an amine, an alcohol, an aldehyde, a ketone, a carboxylic acid, a hydrocarbon, a halogenated hydrocarbon, and water.

17. The method according to claim 15, wherein the sample is gaseous, liquid or solid.

18. A method of testing selected from the group consisting of medical diagnosis, healthcare diagnosis, food quality testing, agricultural testing, security testing for explosives, toxins or harmful chemical substances, and environmental monitoring, the method comprising:
    exposing the sensor of claim 1 to a sample, and
    measuring a presence or an absence of an electrical signal generated by the transducer upon the change of the physical property of the redox active protein, wherein the presence and magnitude of the electrical signal indicates a presence and an amount of a thiol analyte in the sample.

19. The sensor according to claim 1, wherein the redox active protein is selected from the group consisting of thioredoxin, superoxide dismutase, ferredoxin, and cytochrome c oxidase.

20. The sensor according to claim 1, wherein the thiol analyte is cysteine or glutathione.

* * * * *